(12) United States Patent
May et al.

(10) Patent No.: US 6,879,166 B2
(45) Date of Patent: Apr. 12, 2005

(54) MICROWAVE MEASUREMENT OF PHASE EQUILIBRIA

(75) Inventors: Eric F. May, Nedlands (AU); Terry J. Edwards, Nedlands (AU); Anthony G. Mann, Nedlands (AU); Cyril Edwards, Nedlands (AU)

(73) Assignee: University of Western Australia (AU)

( * ) Notice: Subject to any disclaimer, the term of this patent is extended or adjusted under 35 U.S.C. 154(b) by 0 days.

(21) Appl. No.: 10/312,889

(22) PCT Filed: Jun. 28, 2001

(86) PCT No.: PCT/AU01/00784

§ 371 (c)(1),
(2), (4) Date: Feb. 18, 2003

(87) PCT Pub. No.: WO02/01211

PCT Pub. Date: Jan. 3, 2002

(65) Prior Publication Data

US 2003/0155926 A1 Aug. 21, 2003

(51) Int. Cl.$^7$ ................................................ G01R 27/32
(52) U.S. Cl. ........................ 324/636; 324/639; 73/861
(58) Field of Search ................................ 324/633, 636, 324/663, 639; 430/566; 73/861

(56) References Cited

U.S. PATENT DOCUMENTS

| | | | |
|---|---|---|---|
| 3,569,827 A | 3/1971 | Dryden et al. | 324/633 |
| 4,170,135 A | 10/1979 | Booman et al. | 73/290 R |
| 4,729,245 A | 3/1988 | Hansman, Jr. | 73/865 |
| 4,904,928 A | 2/1990 | Lewis | 324/636 |
| 5,389,883 A | 2/1995 | Harper | 324/636 |
| 5,548,217 A * | 8/1996 | Gibson et al. | 324/316 |
| 5,793,216 A | 8/1998 | Constant | 324/639 |

FOREIGN PATENT DOCUMENTS

| | | |
|---|---|---|
| GB | 2120791 A | 12/1983 |
| WO | WO 91/19171 | 12/1991 |
| WO | WO 94/08231 | 4/1994 |

OTHER PUBLICATIONS

"Reebtrant Resonators for Microwave Measurement Units" Romodin et al., 2002 IEEE MTT–S Digest.*
Goodwin, et al., "Reentrant Radio–Frequency Resonator for Automated Phase–Equilibria and Dielectric Measurements in Fluids," Rev. Sci. Instrum., vol. 67, No. 12, Dec. 1996, pp. 4294–4303.
International Search Report Dated Feb. 1, 2002, PCT/AU01/00784.

* cited by examiner

Primary Examiner—N. Le
Assistant Examiner—Walter Benson
(74) Attorney, Agent, or Firm—Ostrolenk, Faber, Gerb & Soffen, LLP

(57) ABSTRACT

A microwave resonator apparatus (35) includes a microwave resonant cavity (36) in fluid communication chamber (38) are dimensioned to ensure high attenuation of resonant electromagnetic fields without impeding fluid flow. The resonant properties of the cavity (36) are therefore completely insensitive to variations in the volume of the pressure chamber (38). The resonator has a specialised reentrant geometry. Consequently, two of the cavity's resonant modes depend sensitively upon the formation and volume of any liquid phase present in the cavity. The apparatus and the method are suitable for measuring dielectric properties and phase envelope of fluid mixtures (such as a gas condensate fluid). The apparatus can be used for making several phase envelope measurements without risk of contamination.

46 Claims, 7 Drawing Sheets

MICROWAVE MEASUREMENT OF PHASE EQUILIBRIA

FIELD OF THE INVENTION

The present invention relates to a microwave technique for measuring the phase behaviour of fluids and relates particularly, though not exclusively, to a microwave apparatus and method for measuring the dielectric properties and phase envelope of natural gas and gas condensate fluids.

BACKGROUND TO THE INVENTION

The role of natural gas and gas condensate fluids in petroleum and hydrocarbon production is one of increasing importance. Natural gas and gas condensates are lean fluids, i.e. they consist predominantly of the low order alkanes—methane, ethane and propane, with decreasing amounts of the higher order alkanes (butane, pentane, hexane etc.). Within a typical reservoir, these lean fluid mixtures exist at high temperatures (~120° C.) and pressures (~350 atm). At these conditions, the fluid is in a single-phase, similar to a dense gas. However the exists a set of (lower) temperatures and pressures at which the fluid mixture exists in two phases at equilibrium. In this two-phase condition, the liquid phase or condensate is rich in the more valuable higher order alkanes.

Natural gas and gas condensate mixtures are extremely complex as they contain a large number of unique hydrocarbon molecules. Hydrocarbons are conventionally referred by the total number of carbon atoms within the molecule and, if feasible, by a letter prefix denoting the isomer. For methane, ethane and propane ($C_1$, $C_2$, $C_3$) there is one possible molecular configuration, for butane ($C_4$) there are two molecular configurations (iso-butane and n-butane) and there are three configurations for pentane ($C_5$). For $C_{10}$ there are 75 possible configurations and for $C_{30}$ there are an estimated 1–2 billion possible configurations of the hydrogen molecule. Table 1 gives a typical composition of a natural gas from Western Australia's North-West Shelf as it enters the pipeline.

The large number of different species in a naturally occurring hydrocarbon mixture makes thermodynamic prediction of its phase behaviour very difficult. The location of a gas condensate's phase boundary in the pressure-temperature (P-T) plane depends sensitively upon the small fractions of the higher order alkanes that it contains. For these reasons, experimental measurement is the only sufficiently accurate method of determining the phase behaviour of a gas condensate. Typically, the aims of such measurements in gas condensates are to determine the fluid's dew point curve and the liquid volume quality lines. FIG. 1 illustrates a typical multi-component phase diagram.

TABLE 1

| Component | Mole Percentage | Component | Mole Percentage |
| --- | --- | --- | --- |
| Nitrogen | 0.941 | Propane | 2.04 |
| Carbon Dioxide | 3.19 | Butanes | 0.886 |
| Methane | 87.04 | Pentanes | 0.205 |
| Ethane | 5.60 | Hexanes + | 0.106 |

The lines within the phase envelope are called quality lines. To the right of the critical point C, the quality lines represent the percentage of the total volume occupied by the liquid phase (1%, 5% and 10% respectively). To the left of the critical point C, the quality lines represent the percentage of the total volume occupied by the gas phase. The phenomenon of retrograde condensation, namely the increase in liquid fraction with decreasing pressure, is a significant feature of the phase behaviour of gas condensate fluids. A few of the numerous examples of the important role that accurate phase behaviour information plays in the production, processing and transport of fluid from the reservoir are discussed below.

As fluid is extracted from a natural gas reservoir, the pressure within the reservoir will drop isothermally along a path similar to abde in FIG. 1. If the pressure drops too far and the upper dew point (b) is reached, retrograde condensation within the reservoir will begin to occur. The heavier, more valuable, hydrocarbons that condense become irretrievably trapped inside the reservoir as they are adsorbed onto the reservoir rock (sandstone) by surface tension and capillary forces. Therefore, to optimise the recovery of the condensate, reservoir engineers employ gas recycling to maintain the reservoir pressure above the fluid's upper dew point pressure. Gas recycling involves the re-injection of lighter, less valuable alkanes, into surrounding re-injection wells pushing the one phase fluid in the reservoir towards the production well and maintaining the reservoir pressure above the upper dew point pressure.

It is essential that the engineers on off-shore platforms and in on-shore processing facilities understand the gas and condensate fluid's phase behaviour. Economic and efficient separation of gases and liquids, extraction of LPG, removal of $CO_2$ and $H_2O$ from product streams, and the production of LNG all depend critically on the fluid's phase behaviour. In particular, LNG in liquid form (formed at −160° C., 1 atm) is the only viable way to export natural gas, as the ships that transport LNG have a fixed volume and only in its liquid form is there sufficient energy density in LNG to justify the cost of shipping.

Overland pipelines transporting natural gas need to ensure that the fluid is always in the single-phase, gas region. Pipelines are maintained at pressures of typically around 80 atm, and are at ambient temperatures. If during the day the condition of the fluid in the pipeline is at point P in FIG. 1, then it is conceivable that at night, the condition of the fluid may approach point Q, a lower dew point. If this lower dew point is reached and sufficient liquid forms in the pipeline, a blockage may develop. The pressure build-up on the up-stream side of the blockage will eventually cause the blockage to move, however this moving mass of liquid will have a momentum which could have potentially disastrous effects on the pipeline and/or the end consumer. Hence, knowledge of the fluid's phase envelope is essential in the design of safe and efficient natural gas transport systems.

Prior art apparatus used to measure the phase behaviour of multi-component hydrocarbon mixtures were designed primarily for use with oil mixtures. The measurements were aimed at detecting the difference between the volume of liquid oil extracted from the oil field at high pressures and the volume of liquid oil remaining at ambient conditions. The measurement of the height of the liquid gives a sufficiently accurate liquid volume, and there is no need for high resolution. However, at most conditions of interest for gas condensate fluids, the liquid volume always comprises a very small fraction of the total volume. Hence, to achieve an accurate measure of this volume, prior art PVT cells for measurement on gas condensate fluids were designed with an "hour-glass" geometry.

The prior art PVT cell system requires high-resolution volumetric pumps and a large overall volume. A sapphire window is located in the "hour-glass" section of the cell, which has a much smaller cross-sectional area than the majority of the cell. Two high-resolution volumetric mercury pumps accurately determine the total volume of the fluid and the relative positions of the bottom and top of the sample. By varying the relative positions, the liquid condensate cam always be positioned within the window and allows a highly accurate measurement of the liquid volume. However, there are significant disadvantages with the conventional PVT cell when used for the measurement of phase equilibria of gas condensate fluids. In particular, as well as being expensive, the equipment is massive, and the large samples required (typically 4000 cm$^3$) take up to 24 hours to come to thermal and chemical equilibrium. Consequently, the measurement of only one or two data points per day is possible, and it therefore takes a long time to collect sufficient data points to develop a phase envelope. Despite their disadvantages, volumetric techniques are the only way currently available to actually measure the volume of liquid.

In 1996 Moldover et al[1] developed a reentrant radio-frequency cavity resonator for automated phase-equilibria and dielectric measurements in fluids. Fluid mixtures were contained within the cavity itself, the fixed volume cavity being filled with a homogenous mixture to the desired density. The temperature was then varied while the pressure and resonant frequency were monitored. The appearance of a new phase in the cavity caused a significant change in the slope of the cavity's resonant frequency-temperature curve. This slope discontinuity is due mostly to the change in the dielectric constant of the portion of the mixture contained within a small annular gap acting as the principal capacitor of the microwave circuit within the cavity. Essentially, Moldover's instrument interrogated the vapour phase of the mixture.

Moldover's cavity clearly demonstrated that accurate and precise measurements of the phase envelope of gas mixtures could be made using microwave techniques, for a small fraction of the cost of the more traditional volumetric techniques. In addition, the cavity enabled highly accurate measurements of molecular properties, such as dielectric constants, polarisability, dipole moment, and its temperature derivative. However, Moldover's resonator had a fixed volume, and therefore different sample densities could only be obtained by varying the amount of gas in the cavity. In the case of heterogeneous, multi-component hydrocarbon mixture it is essential that the sample remain invariant and have constant composition. Furthermore, Moldover's system was only tested on a synthetic binary mixture of composition such that the discontinuous change in the vapour phase was dramatic as the dew point curve was crossed.

SUMMARY OF THE INVENTION

The present invention was developed with a view to providing an improved microwave resonator capable of measuring the dielectric properties and phase envelope for natural gas and gas condensates fluids. However, it will be appreciated that the invention also has application to the measurement of phase equilibria of many other fluids in wider chemical and process industries.

Throughout this specification the term "comprising" is used inclusively, in the sense that there may be other features and/or steps included in the invention not expressly defined or comprehended in the features or steps subsequently defined or described. What such other features and/or steps may include will be apparent from the specification read as a whole.

According to one aspect of the present invention there is provided an apparatus for measuring the phase behaviour of a fluid, the apparatus comprising: [1] A. R. H. Goodwin, J. B. Mehl, M. R. Moldover, Rev. Sci. Instrum., V67, 4294, 1996 an electromagnetic resonant cavity, operating at frequencies up to and including microwave frequencies, with resonant properties sensitive to the presence and volume of a liquid phase;

a pressure chamber of variable volume in fluid communication with the cavity;

a probe for exciting and monitoring the electromagnetic resonances of the cavity;

a pressure sensor and temperature sensor for sensing the pressure and temperature respectively of fluid in the cavity; and, a signal processing means operatively connected to said pressure and temperature sensors and said probe for calculating a phase transition in the fluid within the cavity based on detected changes in the resonant properties of the cavity.

Advantageously said electromagnetic resonant cavity comprises a reentrant geometry designed to facilitate detection and measurement of any liquid phase formed. Preferably the reentrant geometry causes two of the resonant modes of the cavity to depend sensitively on the electric fields in the region where liquid is most likely to form. Alternatively, rather than monitor two modes of the one cavity, the resonances of two distinct microwave cavities in fluid communication are monitored. However, the use of a single reentrant cavity with the particular geometry described below is thought to be most convenient.

According to another aspect of the present invention there is provided an apparatus for measuring the phase behaviour of a fluid, the apparatus comprising:

an electromagnetic resonant cavity, operating at frequencies up to and including microwave frequencies, said cavity being formed with a reentrant geometry having at least two utilised resonant frequency modes in which one resonant mode is employed to facilitate the detection of the onset of formation of a new phase;

a probe for exciting and monitoring the electromagnetic resonances of the cavity;

a pressure sensor and temperature sensor for sensing the pressure and temperature respectively of fluid in the cavity; and, a signal processing means operatively connected to said pressure and temperature sensors and said probe for calculating a phase transition in the fluid within the cavity based on detected changes in the resonant properties of the cavity.

According to a still further aspect of the present invention there is provided a method of measuring the phase behaviour of a fluid, the method comprising the steps of:

detecting changes in the resonant properties of an electromagnetic resonant cavity containing a fluid under various conditions of pressure and temperature;

varying the volume of a pressure chamber in fluid communication with said resonant cavity and/or the temperature of the entire apparatus;

sensing the pressure and temperature of the fluid in the cavity; and, calculating a phase transition of the fluid within the cavity based on the detected changes in the resonant properties of the cavity.

BRIEF DESCRIPTION OF THE DRAWINGS

In order to facilitate a better understanding of the nature of the present invention, a possible embodiment of an apparatus and method for measuring the phase envelope of a gas condensate fluid will now be described in detail by way of example only, with reference to the accompanying drawings, in which.

DETAILED DESCRIPTION OF PREFERRED EMBODIMENTS

Figure 1:
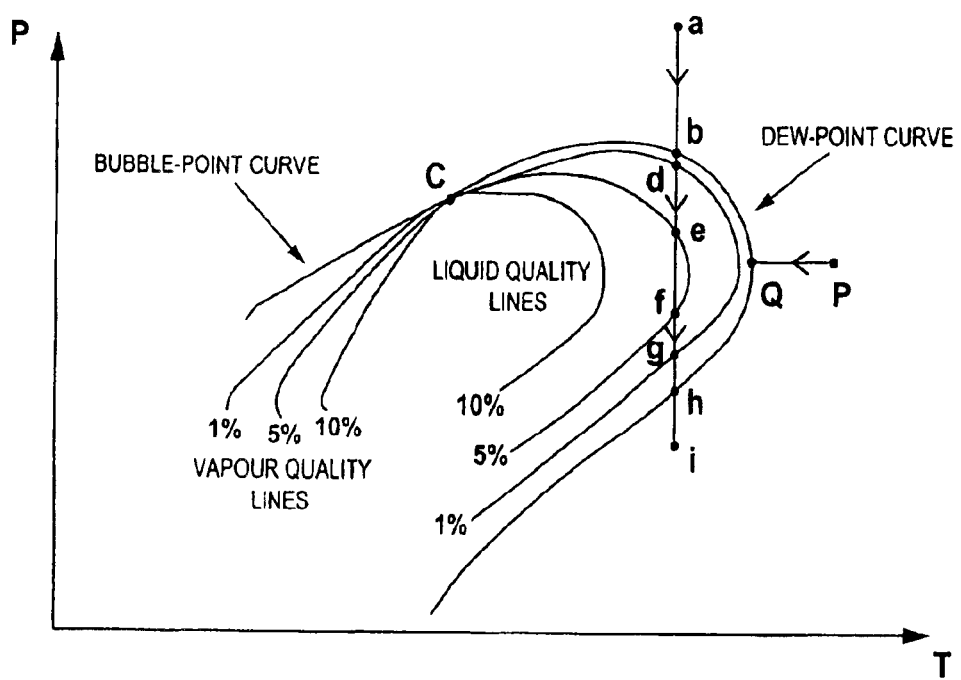
FIG. 1 is a typical phase diagram for a gas condensate fluid.
Figure 2:
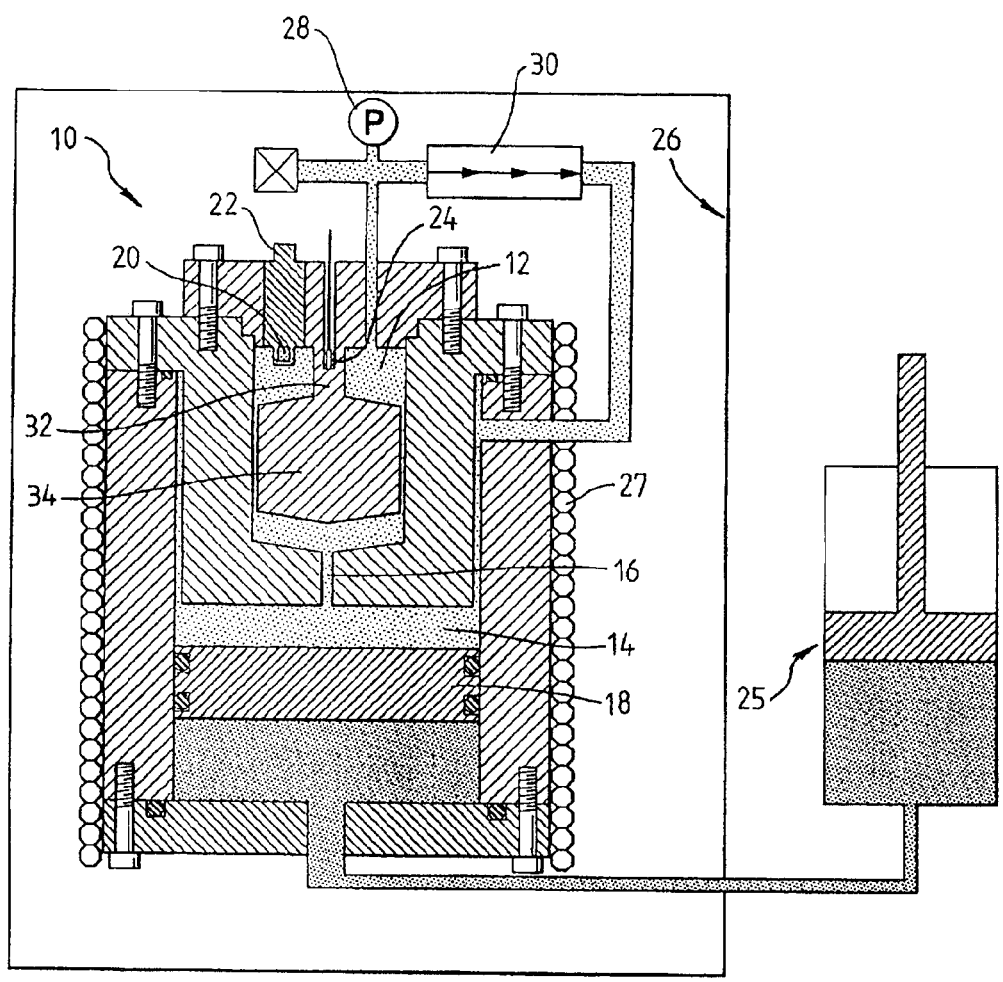
FIG. 2 is a schematic diagram of an experimental system used for testing an embodiment of an apparatus with a variable volume pressure chamber in fluid communication with a microwave cavity in accordance with the present invention.
Figure 3:
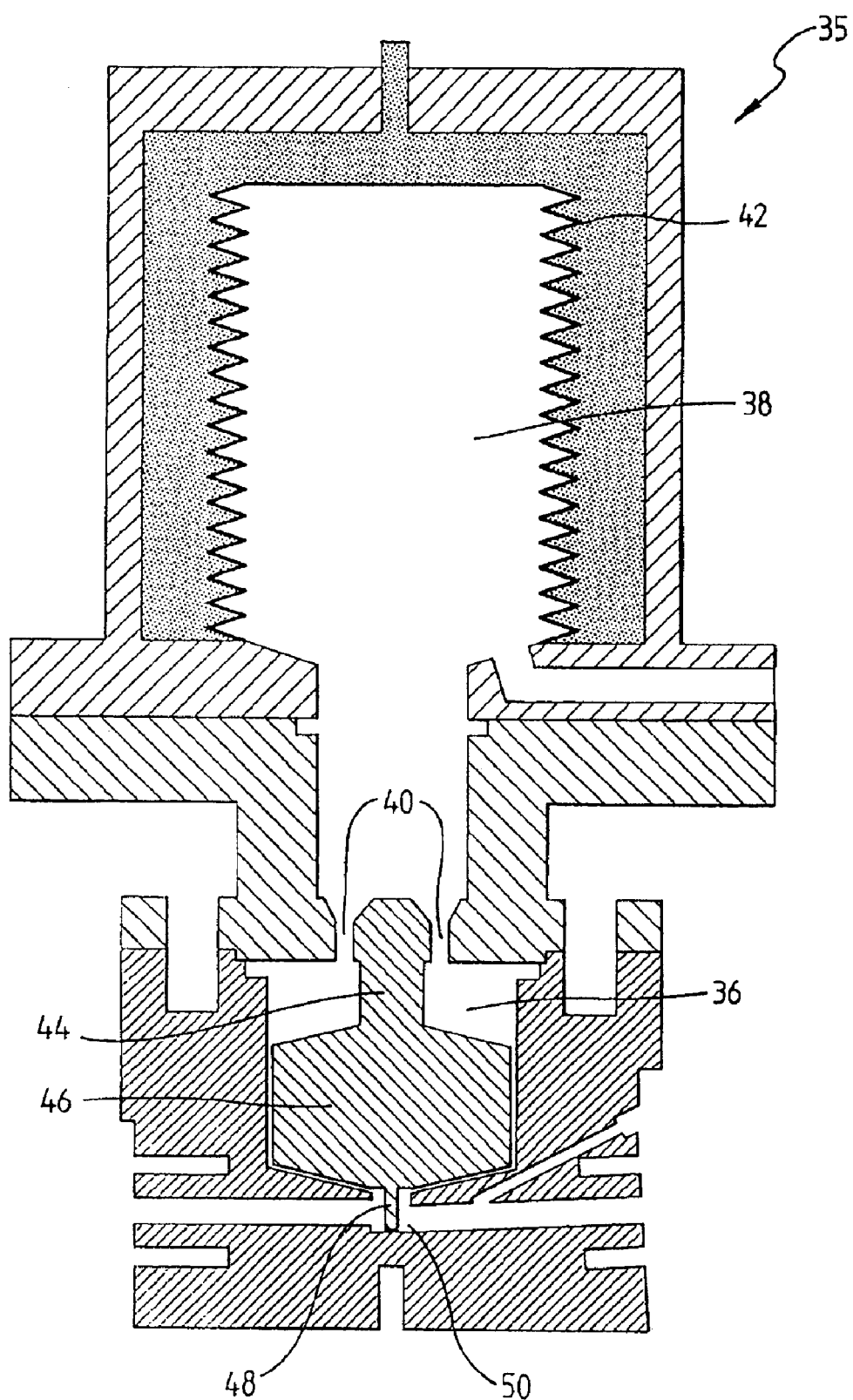
FIG. 3 is a cross-sectional elevation of a resonant cavity and variable volume pressure chamber, which are elements of an embodiment of an apparatus for measuring the phase envelope of a gas condensate fluid in accordance with the present invention.
Figure 4:
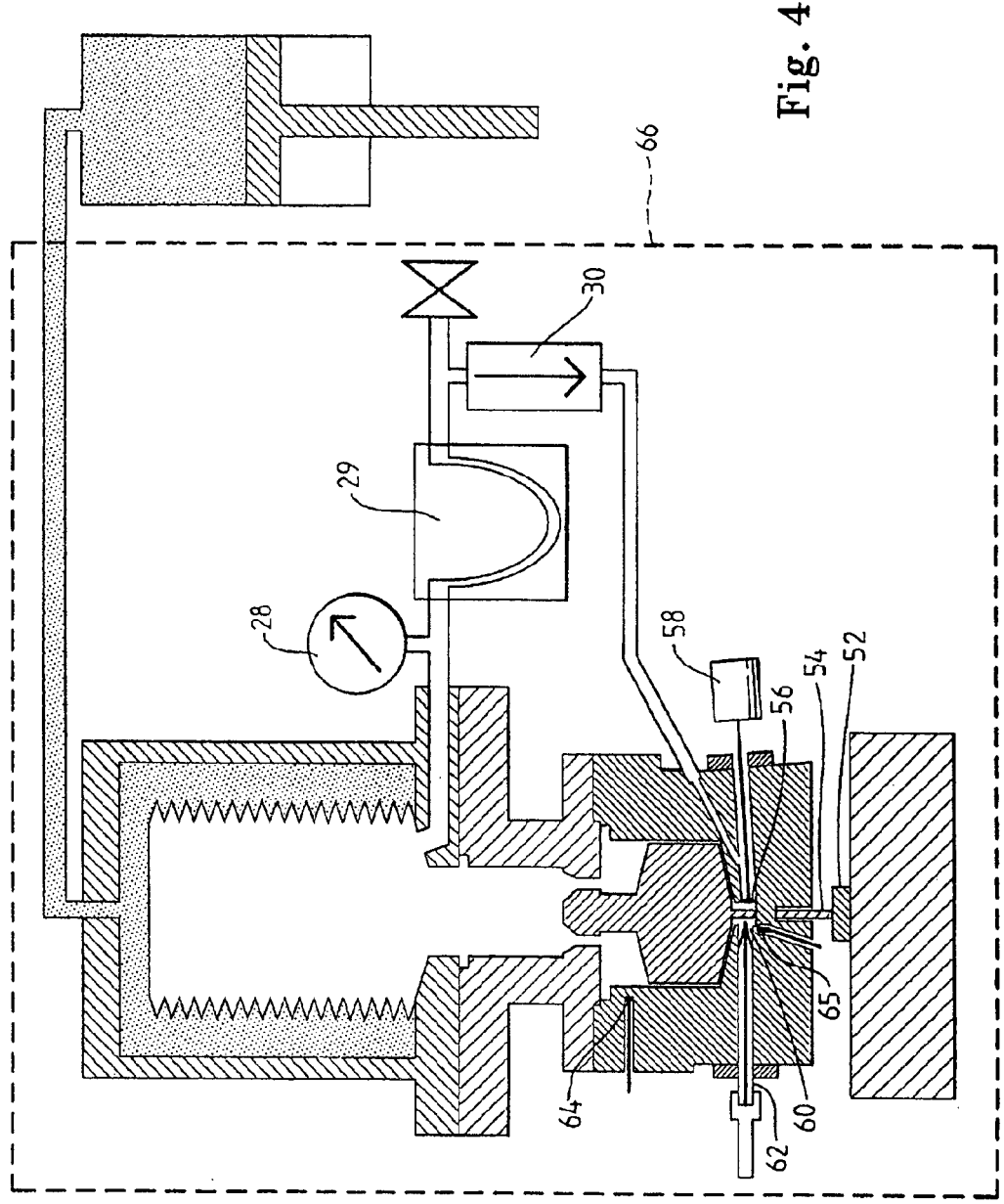
FIG. 4 is a schematic diagram of an embodiment of an apparatus for measuring the phase envelope of a gas condensate fluid in accordance with the present invention, which incorporates the resonant cavity—variable volume pressure chamber illustrated in FIG. 3.

Two embodiments of the present invention are described in detail. The first, illustrated in FIG. 2, is an experimental apparatus 10 that demonstrates the successful combination of a variable volume pressure cylinder 14 in fluid communication with a microwave cavity 12. This embodiment generated most of the experimental data presented in the following section. The second embodiment, illustrated in FIGS. 3 and 4, is a more preferred embodiment. It is based on the first, but has been refined such that it has sufficient sensitivity to detect dew points in lean gas condensates and measure liquid volumes more accurately.

The first embodiment of a variable volume microwave resonator apparatus 10 in accordance with the present invention is illustrated ed in FIG. 2. Tho apparatus consists of a stainless steel pressure cylinder 14 terminated at one end by a brass reentrant cavity 12 and at the other by a floating piston 18. The reentrant cavity 12 is similar to Moldover's, however, the hole 16 in the base of the cavity 12 is dimensioned to ensure high attenuation of radio frequency (rf) fields without impeding fluid flow to or from the pressure cylinder 14. The resonant frequency of the cavity 12 is therefore completely insensitive to variations in the position of the piston 18. The hydraulically driven piston 18 mounted within the pressure chamber 14 allows the total volume occupied by the fluid to be varied.

To determine and track the resonant frequency of the cavity 12, a frequency discriminator circuit is used (not shown). A simpler but more expensive method is to use a vector network analyser to determine the complex scattering parameters of the microwave cavity 12 as a function of frequency. In either case, the resonator is excited by an electromagnetic signal transmitted through or reflected off the cavity 12 via probe(s) 20 attached to glass-to-metal feedthrough(s) 22 soldered into the cavity lid.

A thermistor 24, calibrated against a standard platinum resistance thermometer, is mounted in the thin neck of the cavity 12 and used to monitor the temperature of the apparatus. A resistive heater 27 and fan-forced oven 26 are used to control the system's temperature. Oven 26 and resistive heater 27 are employed to simulate reservoir conditions and would not necessarily be required in a working down-hole embodiment. A sensitive high-pressure transducer 28 is used to measure the pressure. A syringe pump 25 is used to pump hydraulic fluid to the underside of the floating piston 18. A recirculation pump 30 is used to remix samples that have undergone separation into two phases of differing composition; active mixing is preferable for achieving chemical equilibrium and reproducible data. The recirculation pump 30 extracts fluid from the top of the brass cavity 12, and returns it to the pressure cylinder 14. A desktop PC (not shown) with a GPIB card and LabVIEW software is used for data acquisition, frequency tracking and thermal control, and also to provide real-time plots of the resonator's frequency, temperature and pressure.

The microwave resonant cavity 12 is defined by a hollow brass cylindrical section having a top wall and a sloping bottom wall, with a thin central cylindrical neck 32 extending down into the cavity. The neck 32 expands into a bulbous coaxial extension 34 that nearly fills the hollow interior of the cavity. The outer diameter of the bulbous section 34 is approximately 2 mm less than the inner diameter of the outer cylindrical wall, leaving a 1 mm annular gap. The bottom surface of the bulbous extension 34 slopes at the same angle as the bottom wall of the outer cylinder at a separation of about 6 mm.

The basic principle of operation of the microwave resonator 10 can be illustrated by approximating the cavity 12 as a simple LCR circuit. The principal inductance is determined by the thin neck 32 and surrounding toroidal volume. The 1 mm annular gap region determines the principal capacitance. This capacitance is proportional to the dielectric constant, $\epsilon$, of the fluid in the annular gap. From this model the measured resonant frequency, $f_o$, is related to $\epsilon$ according to:

$$f_0 = \frac{f_{vac}}{\sqrt{\varepsilon}} = \frac{1}{\sqrt{\varepsilon}}\left(\frac{1}{2\pi\sqrt{LC_{vac}}}\right)$$

Here, $f_{vac}$ and $C_{vac}$ are the resonant frequency principal capacitance of the evacuated cavity and L is the principal inductance, which is insensitive to the fluid in the cavity. For this embodiment, $f_{vac}$~645 MHz, $C_{vac}$~16 pF and L~4 nH.

More sophisticated models can be used to relate $\epsilon$ and the dimensions of the cavity to $f_o$. Moldover et al. developed an analytical waveguide model that incorporates fringing field estimates. This waveguide model is a significant improvement on the LCR circuit model and predicts resonant frequencies accurate to ±1%. In the preferred method of the present invention, finite element analysis (FEA) is employed to solve the electromagnetic field equations. The precision of the FEA method is effectively limited only by the precision with which the dimensions of the microwave resonator are known.

The second, more preferred embodiment illustrated in FIGS. 3 and 4 is similar to the first embodiment, with refinements necessary to detect dew points in extremely lean gas condensate fluids. The second embodiment consists of a brass microwave resonant cavity 36 in fluid communication with a variable volume pressure cylinder 38. The pressure cylinder 38 is located above the cavity 36; the top flange of the cavity bolting on to the bottom flange of the pressure cylinder. The apertures 40 in the top of the cavity are dimensioned to ensure high attenuation of rf and microwave fields without impeding fluid flow. The resonant properties of the cavity 36 are therefore completely insensitive to variations in the volume of the pressure cylinder 38. A hydraulically driven bellows 42 comprises the internal walls of the pressure cylinder 38. This allows the total volume occupied by the high-pressure fluid to be varied without having to employ any dynamic seals, which are typically elastomeric and have far poorer maximum leak rates than the static, metallic seal's used in this embodiment.

The most significant refinement compared to the first embodiment is the change in the reentrant geometry of the brass resonant cavity 36. Again, a thin central cylindrical neck 44 extends down into the outer cylindrical cavity. The neck 44 then expands into a bulbous coaxial extension 46 that nearly fills the hollow interior of the cavity. A 1 mm annular gap is formed between the bulbous coaxial extension 46 and the cylindrical wall. The bottom surface of the bulbous extension 46 slopes parallel to the bottom wall of the outer cylinder at a separation of 0.5 mm. A 2 mm diameter post 48 centred on the bottom of the bulbous coaxial extension 46 extends into a 6 mm diameter well 50 centred in the bottom wall of the outer cylinder. The post 48 terminates 0.2 mm above the bottom of the well 50.

This reentrant geometry results in the microwave cavity having two resonant modes that depend very sensitively upon the formation and volume of a liquid phase. The vacuum resonant frequencies of these two resonant modes are approximately $f_{vac}^{low} \approx 460$ MHz and $f_{vac}^{high} \approx 6.8$ GHz. The frequency of the high resonant mode is almost completely determined by the post—well 48 —50 region of the cavity whereas the frequency of the low resonant mode is determined primarily by the bulbous coaxial extension 46. A similar system could in fact use two distinct cavities in fluid communication with each other, and would essentially be the same as the one described here although operation of such a system would be less convenient.

The frequency of the high resonant mode is extremely sensitive to the dielectric constant of the fluid in the 0.2 mm gap between the post 48 and well 50 bottom. Because of the high frequency of this mode, FEA has shown that any liquid phase which forms in this gap would result in a signal approximately 4000 times greater than the signal generated by a similar amount of liquid present in the first embodiment 10 (or Moldover's cavity). Three mechanisms, collectively referred to as "dew focussing" techniques, are employed in this preferred embodiment to ensure that the first droplets of any liquid phase formed in the apparatus will be located in the 0.2 mm gap. Firstly, a thermoelectric cooler 52 in contact with a 3 mm diameter rod of silver 54, cools the brass immediately below the bottom of the well 50. As a result the temperature of the 0.2 mm gap (the region of highest electric field intensity) can be lowered relative to the rest of the apparatus. Experimental tests on the preferred embodiment have achieved temperature reductions of 0.5° C. of the 0.2 mm gap relative to the rest of the apparatus over a sustained period of time. Secondly, the re-circulation pump 30 described in the first embodiment is employed as the active mixing system. The re-circulation pump extracts fluid from the variable volume pressure chamber 38 and returns it to the 0.2 mm gap. Finally, the gap is the lowest point of the entire apparatus and all internal surfaces are sloped to allow drainage to this low point. These three dew focussing mechanisms ensure that the high sensitivity of the preferred embodiment to the presence of any liquid phase is realised.

The spatial distribution of the electric fields within these microwave systems is largely independent of the dielectric constant(s) of the fluid it contains. Consequently, the shape of the frequency vs (temperature or pressure) curve across the two-phase region has features that are invariant of the fluid, as long as there is a significant distinction between the liquid and vapour phases. (This is illustrated in the Experimental Results below.) These invariant features of the curve allow the location of the liquid—vapour interface to be inferred, which gives a measure of the liquid volume. The purpose of the low frequency resonant mode in the preferred embodiment is to provide a measure of the liquid volume in the microwave cavity once a significant amount of the liquid phase is present. The most precise measurements of the liquid volume are possible as the liquid—vapour interface passes the "corners" of the bulbous coaxial extension 46.

To ensure that the liquid volume measurements are accurate as well as precise, a check valve 56 is located at the end of the re-circulation path located in the wall of the well 50. An external stepper-motor 58 is employed to open and close the check valve 56. The closing of the check valve 56 is timed with the (final) upstroke of the recirculation pump 30. This ensures that no liquid phase remains in the circulation loop and that liquid does not egress from the cavity 36 back into the loop.

In the preferred embodiment, both of the electromagnetic resonances are excited using an electric field probe 60 located in the wall of the well 50, opposite the check valve 56. A high-pressure feedthrough 62, approximately 40 mm in length, connects the probe 60 to either a frequency discriminator circuit or vector network analyser (not shown). A possible modification to the preferred embodiment would be to place a second probe near the top of the cavity, allowing the cavity's transmission scattering parameters to be measured by the network analyser as well as its reflection scattering parameters. The advantage of this modification is that the network analyser could then be used (in time domain reflectometry mode) to detect impedance discontinuities along the waveguides. This would provide another, independent means of the location of any liquid—vapour interface and hence the liquid volume.

A sensitive high-pressure transducer 28 monitors the system's pressure. Several thermistors 64 are employed to monitor the temperature of the system at various locations. At least one of these thermistors 65 is located as close as possible to the bottom of the well 50 to monitor and control the reduction in the temperature of the 0.2 mm gap. In the preferred embodiment, the thermoelectric cooler 52 and the thermistor 65 monitoring the temperature of the 0.2 mm gap comprises one of three independent thermal control systems. A resistive heater (similar to 27 in the first embodiment) and a constant temperature fluid jacket or oven 66 are the other two systems. These independent control systems ensure that the temperature of the 0.2 mm gap is the lowest in the entire apparatus.

A high-pressure densimeter 29 can be incorporated into the circulation loop, as shown in FIG. 4, such that it measures the density of the fluid extracted from the variable volume pressure chamber 38. An initial measurement of the density of a single-phase fluid, $\rho^{init}$, using this device, together with knowledge of the initial system volume, $V_{total}^{init}$, determines the mass of sample, m, contained in the system. The volume, $V_{total}$, can then be varied and the resulting bulk density, $\rho$, inferred. Once the fluid has separated into two phases, the densimeter 29 can be used to provide a measure of the vapour phase density, $\rho_v$. Mass and volumetric balance equations can then be applied to determine the liquid phase density, $\rho_l$, and vapour mass fraction, v.

$$V_v = V_{total} - V_l$$

$$m = \rho^{initial} V_{total}^{initial}$$

$$m_v = \rho_v V_v$$

$$m_l = m - m_v$$

$$\rho_l = \frac{m_l}{V_l}$$

$$v = \frac{m_v}{m}$$

Further thermodynamic information about the two-phase fluid can be estimated if some assumptions are made. For example, consider a binary mixture of known bulk composition (mass fractions $z_1$ and $z_2$) in the two-phase state being measured by the variable volume microwave system. The composition of the liquid phase (mass fractions $x_1$ and $x_2$), the composition of the vapour phase (mass fractions $y_1$ and $y_2$), the dielectric constant of the liquid phase, $\epsilon_l$, and the dielectric constant of the vapour phase $\epsilon_v$, can be estimated by solving the following system of equations:

$$x_1 + x_2 = 1$$

$$y_1 + y_2 = 1$$

$$z_1 = v y_1 + (1-v) x_1$$

$$\frac{\epsilon_v - 1}{\epsilon_v + 2} = \rho_v (a_1 y_1 + a_2 y_2)$$

$$\frac{\epsilon_l - 1}{\epsilon_l + 2} = \rho_l (a_1 x_1 + a_2 x_2)$$

$$\epsilon_{eff} = \epsilon_l g + \epsilon_v (1-g)$$

Here, $a_1$ and $a_2$ are the polarisabilities per unit mass of the two pure component fluids at the temperature and pressure of the mixture and g is taken to be a monotonic, normalised function of the liquid volume, independent of the fluid. The function g is derived from the frequency—density curve of a calibration fluid in two phases as it fills the cavity 36. Finally, $\epsilon_{eff}$ is an effective dielectric constant of the two phases. It is determined from the measured resonant frequency and the vacuum resonant frequency corresponding to the conditions of pressure and temperature of the measurement. The exact relationship depends on the model being employed; for example for the simple LCR circuit model the following relation would be used.

$$\epsilon_{eff} = \left(\frac{f_{vac}}{f_0}\right)^2$$

Experimental Results

Figure 5:
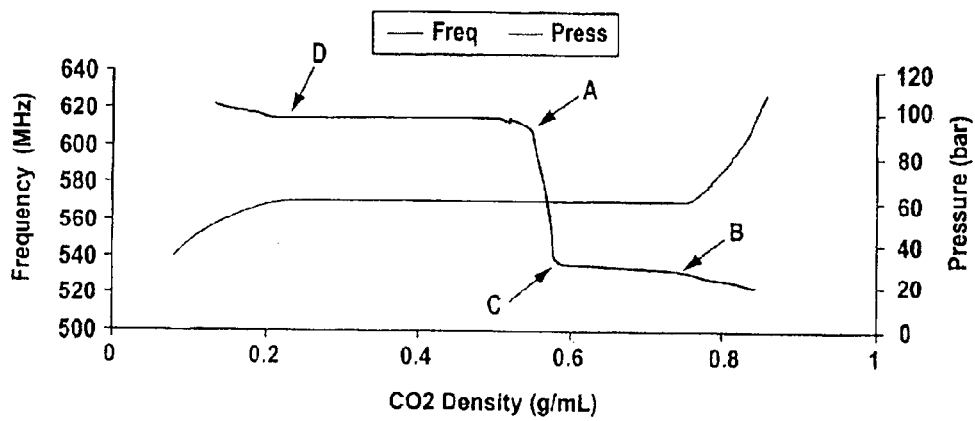
FIG. 5 illustrates graphically the frequency signature of pure carbon dioxide measured using an experimental system similar to that illustrated in FIG. 2.

FIG. 5 illustrates graphically the frequency "signature" (frequency vs density curve) of pure $CO_2$ fluid as it was compressed across the two-phase region using the apparatus 10 illustrated in FIG. 2. The frequency signature demonstrates that microwave systems can measure phase volumes in addition to phase boundaries. The changes in its slope at points D and B correspond to the dew and bubble points of the isotherm. The slope changes in the frequency curve at points A and C are of more significance, since in a pure fluid the phase change can be readily identified from the slope of the pressure versus density curve. These slope changes identify the location of the liquid phase within the cavity 12 as they correspond to changes in the capacitance region that is being filled with liquid. The section of the curve with the greatest slope corresponds to the liquid filling the 1 mm-annular gap that comprises the principal capacitance of the cavity 12. For a pure fluid, across the two-phase region, $\epsilon_v$ and $\epsilon_l$ are constants, and thus pure $CO_2$ would be an appropriate calibration fluid for determining the value of g as a function of liquid volume.

Figure 6:
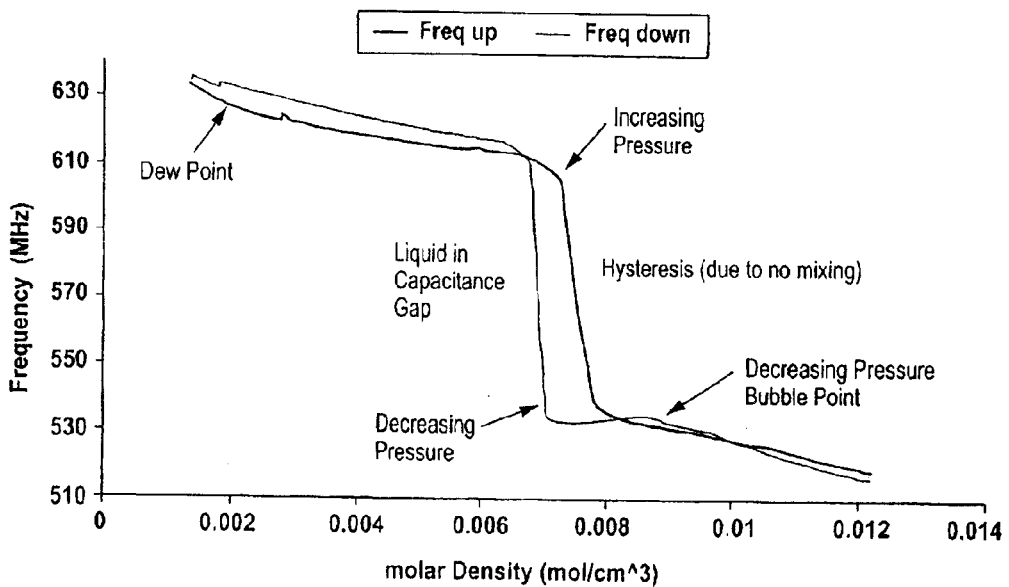
FIG. 6 illustrates graphically the frequency signature of a close boiling binary fluid mixture measured using an experimental system similar to that illustrated in FIG. 2.

FIG. 6 shows the frequency signature of a close boiling binary mixture consisting of 49.5% $C_3H_8$ and 50.5% $CO_2$, which was first isothermally compressed, and then isothermally expanded, at 310.00 K, across the two-phase region. In addition to the slope changes corresponding to the dew and bubble points, the large slope changes as liquid fills the cavity 12 provide a measure of the phase volumes. The similarity of the frequency signature for the binary mixture to the frequency signature for pure $CO_2$ illustrates that the spatial distribution of the electric field is essentially independent of the fluid in the cavity.

The hysteresis exhibited in the binary mixture's frequency signature as the direction along the isotherm is reversed occurred because the mixing pump 30 was not employed during the scan, and once the fluid entered the two-phase region a compositional stratification resulted. To verify this stratification, at the conclusion of the experiment, samples were taken from the resonator 10 and analysed by a gas chromatograph. The fraction of $C_3H_8$ was 0.50, 0.56 and 0.66 at the "top"; "middle" and "bottom" of the resonator respectively. Although the sampling method was somewhat crude, the results indicate that the liquid phase, richest in $C_3H_8$, fell to the bottom of the resonator while the fluid was in the two-phase region. These data clearly illustrate the need to employ an active mixing system.

A constant volume resonator with the same reentrant geometry as the apparatus illustrated in FIG. 3, but without the variable volume 38, constitutes another embodiment of this invention as it could be used to detect sensitively dew points in gas condensate fluids along constant volume pathways. Such a resonator, with an internal volume of 34 cm³ was incorporated into an experimental system similar to that illustrated in FIG. 4 and was then used to detect the dew point of a gas condensate fluid, the composition of which is given in Table 2. The constant volume apparatus was filled at 62.5° C. to 73 bar of the gas condensate; the sample cylinder and fill lines were all heated to well above this temperature, which itself is far from the dew point curve of the fluid. The apparatus was then isolated and cooled along a constant volume pathway towards the dew point. The Peng-Robinson Equation of State predicts a dew point temperature of 38° C. for this isochore. The temperature of the apparatus was reduced in decrements of between 2.5° C. and 1° C. After each temperature change, the pressure, temperature and frequencies of the apparatus were monitored. When they became constant to within pre-set limits (0.01° C., 0.003 bar, 0.002 MHz and 0.01 MHz) over a half-hour period, the system was deemed to have achieved equilibrium. After a minimum of half an hour at equilibrium, the temperature of the apparatus would be decremented again. The three independent thermal control systems were utilised to ensure that the temperature of the 0.2 mm gap was always 0.2° C. lower than any other part of the apparatus.

TABLE 2

| Component | Mole Percentage | Component | Mole Percentage |
|---|---|---|---|
| Nitrogen | 2.07 | Propane | 7.89 |
| Carbon Dioxide | 1.33 | Butanes | 4.44 |
| Methane | 70.11 | Pentanes | 0.94 |
| Ethane | 12.70 | Hexanes | 0.52 |

Figure 7:
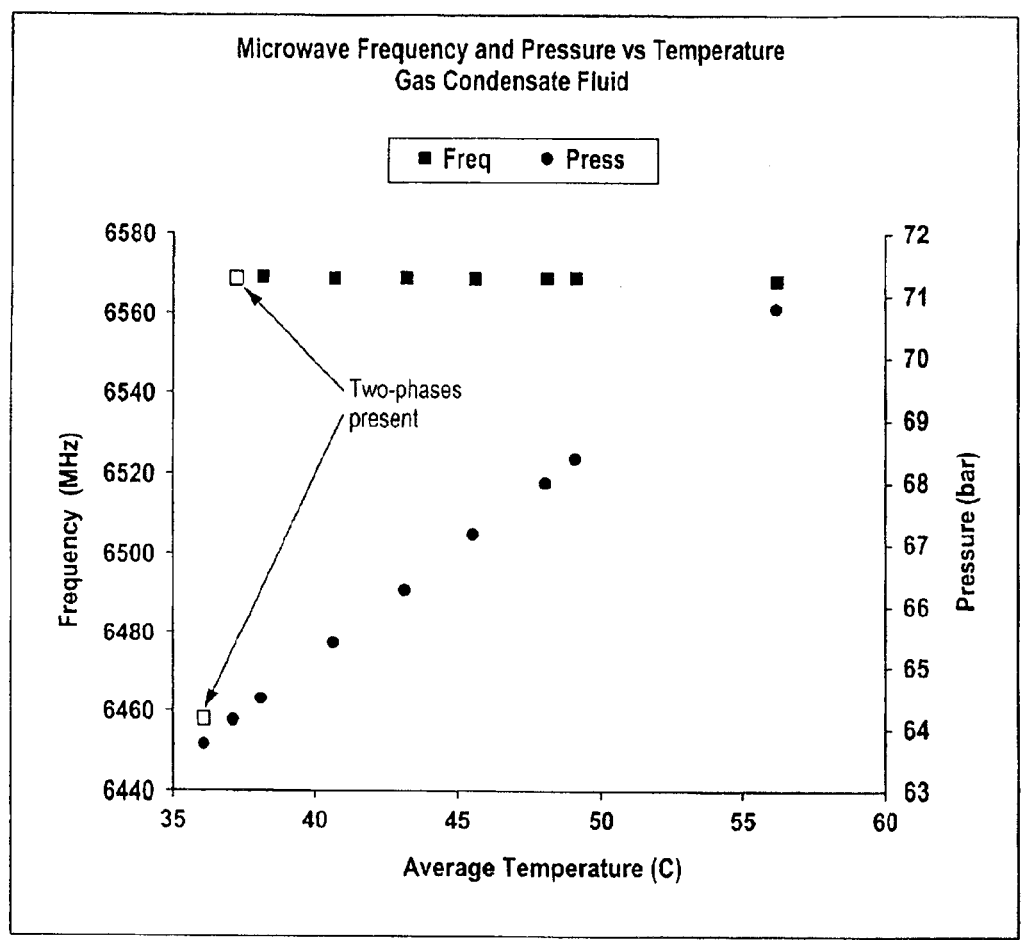
FIG. 7 illustrates graphically the measured microwave frequency of the resonator illustrated in FIG. 3 together with the pressure of the gas condensate fluid in the resonator as it is cooled through the dew point; and, FIG. 8 illustrates graphically the microwave frequencies in FIG. 7 in the vicinity of the dew point.

FIG. 7 shows a plot of the microwave frequency of the resonator (square points) as a function of temperature. Also shown is the measured pressure at the corresponding temperature. The hollow squares correspond to frequencies measured whilst in the two-phase condition. The frequency measured at the coolest temperature (36.1° C.) is more than 110 MHz below the frequency measured at 37.1° C. This illustrates the high sensitivity of the preferred embodiment. The Peng-Robinson equation of state predicts a liquid volume of less than 0.2 cm$^3$ at this pressure and temperature; this amount of liquid has caused a frequency shift more than ten thousand times greater than the resolution with which the microwave frequency can be measured.

Figure 8:
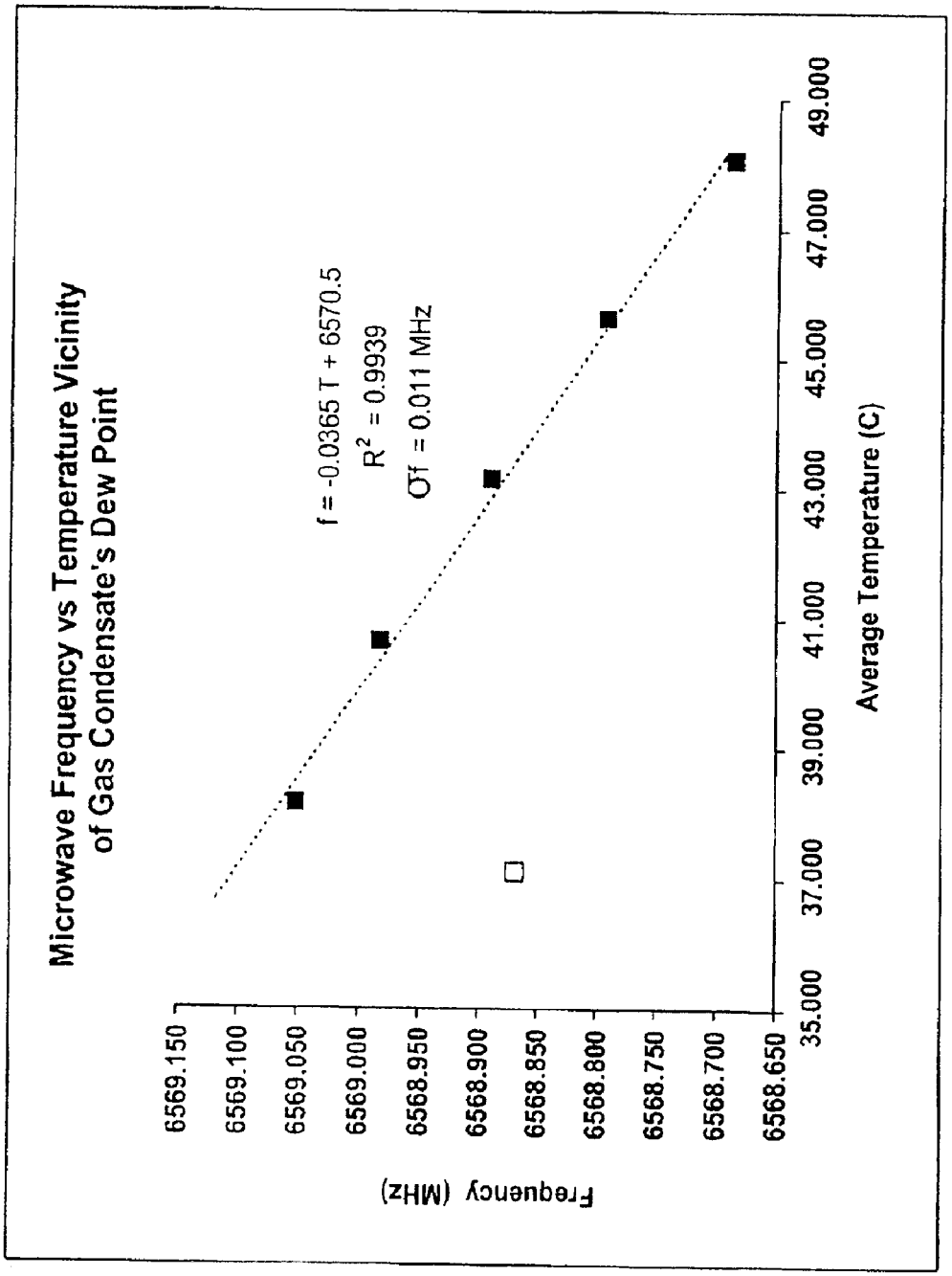

FIG. 8 shows the measured microwave frequencies in the vicinity of the dew point. The solid squares represent the frequencies measured while the fluid was in the single phase. Least squares linear regression illustrates that the single phase frequencies vary with temperature at about −0.04 MHz/° C. The measured frequency at 37.14° C. (hollow square) clearly does not lie on the single phase line; the deviation exhibited by this point is caused by the formation of a very small amount of liquid in the 0.2 mm gap. From this experimental data we estimate that the dew point temperature is 37.15±0.20° C. along this isochore. This error bound is conservative and could be improved by taking more data in the vicinity of the dew point.

FEA modelling of the resonator can be combined with the gas condensate experimental data shown here to estimate the smallest liquid volume that this apparatus can unambiguously detect. For a typical hydrocarbon liquid, ($\epsilon_r$~1.6), this constant volume apparatus can detect a volume of less than 5×10$^{-7}$ cm$^3$ or, equivalently, it can detect 15 parts per billion, by volume, of a liquid phase.

Now that possible embodiments of the apparatus and method for measuring the phase envelope of a gas condensate fluid have been described in detail, it will be apparent that the described system has a number of advantages over the prior art (volumetric and microwave) techniques:

(i) it facilitates the measurement of multiple phase transitions with one sample of the fluid mixture, without risk of contamination of the sample;
(ii) it allows a microwave based system to make the equivalent set of measurements (phase envelope and liquid volumes) in an analogous fashion to those made by volumetric prior art systems;
(iii) only a small sample volume is required and equilibrium conditions can be achieved within a relatively short time, facilitating rapid measurements;
(iv) it has sufficient sensitivity to detect dew points in ultra lean gas condensate and natural gas fluids;
(v) it could be combined with a high pressure densimeter to estimate the phase compositions of certain mixtures;
(vi) being compact in construction, the apparatus can be lowered into a well to allow in situ measurement of the phase equilibria of a gas condensate fluid;
(vii) it is of robust design, and can be flange-mounted and connected to piping in a gas processing plant, and thence used for in-situ measurements of the dew point of process fluids being transported within the pipe; and,
(viii) the apparatus is of relatively inexpensive construction and employs readily available electronic systems to perform data processing and analysis.

Numerous variations and modifications will suggest themselves to persons skilled in the appropriate arts, in addition to those already described, without departure from the basis inventive concepts. For example, for in situ measurements the apparatus and method would include a facility for automatically retrieving a fluid from an adjacent reservoir or pipeline. All such variations and modifications are to be considered within the scope of the present invention, the nature of which is to be determined from the foregoing description and the appended claims.

What is claimed is:

1. An apparatus for measuring the phase behavior of a fluid, the apparatus comprising:
   an electromagnetic resonant cavity, operating at frequencies up to and including microwave frequencies, with resonant properties sensitive to the presence and volume of a liquid phase;
   a pressure chamber of variable volume in fluid communication with the cavity;
   a probe for exciting and monitoring the electromagnetic resonance of the cavity;
   a pressure sensor and temperature sensor for sensing the pressure and temperature respectively of fluid in the cavity; and
   a signal processor operatively connected to said pressure and temperature sensors and said probe for calculating a phase transition in the fluid within the cavity based on detected changes in the resonant properties of the cavity.

2. An apparatus for measuring the phase behavior of a fluid as defined in claim 1, wherein said electromagnetic resonant cavity is formed with a reentrant geometry having at least two utilized resonant frequency modes in which one resonant mode is employed to facilitate the detection of the onset of formation of a new phase.

3. An apparatus for measuring the phase behavior of a fluid, as defined in claim 2, wherein one or more regions of high electric field intensity are provided within the cavity which are positioned such that any liquid phase formed will drain into one of said regions or that any vapor phase formed will float into one of said regions.

4. An apparatus for measuring the phase behavior of a fluid, as defined in claim 3, wherein the reentrant geometry of the cavity is such that it forms one or more gaps resulting in regions of vary high electric field intensity.

5. An apparatus for measuring the phase behavior of a fluid, as defined in any one of claims 1 to 4, wherein said electromagnetic resonant cavity comprises a plurality of distinct, independent electromagnetic cavities in fluid communication.

6. An apparatus for measuring the phase behavior of a fluid as defined in claim 2, wherein a particular resonant frequency mode is untilized primarily to obtain liquid volume measurements from the invariant parts of a frequency signature (frequency vs temperature/pressure/density curve) of the fluid.

7. An apparatus according to claim 2, wherein other of said at least two resonant frequency modes are used to:
   infer liquid volume; or increase reliability of information determined from said one resonant mode; or both infer liquid volume and increase reliability of information determined from said one resonant mode.

8. An apparatus for measuring the phase behavior of a fluid as defined in claim 3, wherein the temperature of all parts of the apparatus is controlled within set bounds by a thermal control system.

9. An apparatus for measuring the phase behavior of a fluid as defined in claim 8, wherein a cooling device or heater is provided proximate said one or more regions of high electric field intensity for cooling or heating said region(s) relative to the remainder of the apparatus, and promoting the formation of a new phase in said region(s).

10. An apparatus for measuring the phase behavior of a fluid as defined in claim 3, further comprising an active fluid mixing system for actiely mixing fluid in the apparatus, said active fluid mixing system comprising a recirculation pump and a circulation loop which insure that the fluid circulates through the region(s) of high electric field intensity.

11. An apparatus for measuring the phase behavior of a fluid as defined in claim 10, wherein a fluid check valve is provided in said circulation loop at the point where the loop is connected to the cavity for insuring that all the liquid phase is confined within the cavity when the recirculation pump is switched off.

12. An apparatus for measuring the phase behavior of a fluid as defined in claim 1, wherein the temperature of all parts of the apparatus is controlled within set bounds by a thermal control system.

13. An apparatus for measuring the phase behavior of a fluid as defined in claim 1, further comprising an active fluid mixing system for actively mixing fluid in the apparatus to insure that a vaoor phase and a liquid phase are kept in a state of chemical equilibrium in the apparatus.

14. An apparatus for measuring the phase behavior of a fluid as defined in claim 1, wherein said signal processor nerforms time domain reflectometry thereby permitting the location of any liquid vavor interface to be determined by measurements of impedance discontinuities.

15. An apparatus for measuring the phase behavior of a fluid as defined in claim 1, wherein the volume of the pressure chamber is varied by means of a bellows or piston.

16. An apparatus for measuring the phase behavior of a fluid as defined in claim 1, wherein the pressure chamber or resonant cavity is in fluid communication with a high-pressure densimeter, allowing independent determination of the bulk density of one of the phases when the fluid is in a two phase state.

17. An apparatus of measuring the phase behavior of a fluid, the apparatus comprising:

an electromagnetic resonant cavity, operating at frequencies up to and including microwave frequencies, said cavity being formed with a reentrant geometry having at least two utilized resonant frequency modes in which one resonant mode is employed to facilitate the detection of the onset of formation of a new phase;

a probe for exciting and monitoring the electromagnetic resonance of the cavity;

a pressure sensor and temperature sensor for sensing the pressure and temperature respectively of fluid in the cavity; and a signal processor operatively connected to said pressure and temperature sensors and said probe for calculating a phase transition in the fluid within the cavity based on detected changes in the resonant properties of the cavity.

18. An apparatus for measuring the phase behavior of a fluid as defined in claim 17, wherein one or more regions of high electric field intensity are provided within the cavity which are positioned such that any liquid phase formed will drain into one of said regions or that any vapor phase formed will float into one of said regions.

19. An apparatus for measuring the phase behavior of a fluid, as defined in claim 18, wherein the reentrant geometry of the cavity is such that it forms one or more sub-millimeter gaps resulting in regions of very high electric field intensity.

20. An apparatus for measuring the phase behavior of a fluid, as defined in any one of claims 17 to 19, wherein said electromagnetic resonant cavity comprises a plurality of distinct, independent electromagnetic cavities in fluid communication.

21. A method of measuring the phase behavior of a fluid, the method comprising the steps of:

detecting changes in the resonant properties of an electromagnetic resonant cavity containing a fluid under various conditions of pressure and temperature;

varying the volume of a pressure chamber in fluid communication with said resonant cavity and/or the temperature of the entire apparatus;

sensing the pressure and temperature of the fluid in the cavity; and calculating a phase transition of the fluid within the cavity based on the detected changes in the resonant properties of the cavity.

22. A method of measuring the phase behavior of a fluid as defined in claim 21, the method further comprising the step of:

actively mixing the fluid to insure that a vapor phase and a liquid phase are kept in a state of chemical equilibrium in the cavity.

23. A method of measuring the phase behavior of a fluid as defined in claim 22, the method further comprising the step of:

cooling or beating a region of the cavity having a high electric field intensity in order to promote the formation of a new phase in said region.

24. A method of measuring the phase behavior of a fluid as defined in claim 21, the method further comprising the step of:

measuring the bulk density of the fluid and the density of one of the phases, which may be used to determine or obtain additional thermodynamic information from the measurements, such as the phase compositions of a mixture.

25. A method of measuring the phase behavior of a fluid as defined in claim 21, the method further comprising the step of:

measuring the location of impedance discontinuities within the cavity in order to determine the position of any liquid vapor interface and hence the liquid volume.

26. A method of measuring the phase behavior of a fluid as defined in claim 21, the method further comprising the step of:

using the invariant features of the frequency signature (frequency vs temperature/pressure/density curve) of the fluid to calculate the liquid volume present.

27. An apparatus for measuring the phase behavior of a fluid, the apparatus comprising:

an electromagnetic resonant cavity, operating at frequencies up to and including microwave frequencies, with resonant properties sensitive to the presence and volume of a liquid phase, said electromagnetic resonant cavity formed with a reentrant geometry having at least two utilized resonant frequency modes in which one resonant mode is employed to facilitate the detection of the onset of formation of a new phase, said cavity further provided with one or more regions of high electric field intensity that are positioned such that any liquid phase formed will drain into one of said regions or that any vapor phase formed will float into one of said regions;

a pressure chamber of variable volume in fluid communication with the cavity;

a probe for exciting and monitoring the electromagnetic resonance of the cavity;

a pressure sensor and temperature sensor for sensing the pressure and temperature respectively of fluid in the cavity; and a signal processor operatively connected to said pressure and temperature sensors and said probe for calculating a phase transition in the fluid within the cavity based on detected changes in the resonant properties of the cavity.

28. An apparatus for measuring the phase behavior of a fluid, as defined in claim 27, wherein the re-entrant geometry of the cavity is such that it forms one or more sub-millimeter gaps resulting in regions of very high electric field intensity.

29. An apparatus for measuring the phase behavior of a fluid, as defined in claim 27, wherein said electromagnetic resonant cavity comprises a plurality of distinct, independent electromagnetic cavities in fluid communication.

30. An apparatus for measuring the phase behavior of a fluid as defined in claim 27, wherein the temperature of all parts of the apparatus is controlled within set bounds by a thermal control system.

31. An apparatus for measuring the phase behavior of a fluid as defined in claim 27, wherein a cooling device or heater is provided proximate said one or more regions of high electric field intensity for cooling or heating said region(s) relative to the remainder of the apparatus, and promoting the formation of a new phase in said region(s).

32. An apparatus for measuring the phase behavior of a fluid as defined in claim 27, further comprising an active fluid mixing system for actively mixing fluid in the apparatus to insure that a vapor phase and a liquid phase are kept in a state of chemical equilibrium in the apparatus.

33. An apparatus for measuring the phase behavior of a fluid as defined in claim 27, further comprising an active fluid mixing system for actively mixing fluid in the apparatus, said active fluid mixing system comprising a recirculation pump and a circulation loop which insure that the fluid circulates through the region(s) of high electric field intensity.

34. An apparatus for measuring the phase behavior of a fluid as defined in claim 33, wherein a fluid check valve is provided in said circulation loop at the point where the loop is connected to the cavity for insuring that all the liquid phase is confined within the cavity when the recirculation pump is switched off.

35. An apparatus for measuring the phase behavior of a fluid as defined in claim 27, wherein said signal processor performs time domain reflectometry thereby permitting the location of any liquid-vapor interface to be determined by measurements of impedance discontinuities.

36. An apparatus for measuring the phase behavior of a fluid as defined in claim 27, wherein a particular resonant frequency mode is utilized primarily to obtain liquid volume measurements from the invariant parts of a frequency signature (frequency vs temperature/pressure/density curve) of the fluid.

37. An apparatus for measuring the phase behavior of a fluid as defined in claim 27, wherein the volume of the pressure chamber is varied by means of a bellows or piston.

38. An apparatus for measuring the phase behavior of a fluid as defined in claim 27, wherein the pressure chamber or resonant cavity is in fluid communication with a high pressure densimeter, allowing independent determination of the bulk density and the density of one of the phases when the fluid is in a two-phase state.

39. An apparatus according to claim 27, wherein other of said at least two resonant frequency modes are used to:
infer liquid volume; or increase reliability of information determined from said one resonant mode; or both infer liquid volume and increase reliability of information determined from said one resonant mode.

40. An apparatus for measuring the phase behavior of a fluid, the apparatus comprising:

an electromagnetic resonant cavity, operating at frequencies up to an including microwave frequencies, said cavity being formed with a reentrant geometry having at least two utilized resonant frequency modes in which one resonant mode is employed to facilitate the detection of the onset of formation of a new phase, the cavity provided with one or more regions of high electric field intensity that are positioned such that any liquid phase formed will drain into one of said regions or that any vapor phase formed will float into one of said regions;

a probe for exciting and monitoring the electromagnetic resonances of the cavity;

a pressure sensor and temperature sensor for sensing the pressure and temperature respectively of fluid in the cavity; and, a signal processor operatively connected to said pressure and temperature sensors and said probe for calculating a phase transition in the fluid within the cavity based on detected changes in the resonant properties of the cavity.

41. An apparatus for measuring the phase behavior of a fluid, as defined in claim 40, wherein the re-entrant geometry of the cavity is such that it forms one or more sub-millimeter gaps resulting in regions of very high electric field intensity.

42. An apparatus for measuring the phase behavior of a fluid, as defined in claim 40, wherein said electromagnetic resonant cavity comprises a plurality of distinct, independent electromagnetic cavities in fluid communication.

43. A method of measuring the phase behavior of a fluid, the method comprising the steps of:

detecting changes in the resonant properties of an electromagnetic resonant cavity containing a fluid under various conditions of pressure and temperature;

varying the volume of a pressure chamber in fluid communication with said resonant cavity and/or the temperature of the entire apparatus;

actively mixing the fluid to insure that a vapor phase and a liquid phase are kept in a state of chemical equilibrium in the cavity;

sensing the pressure and temperature of the fluid in the cavity;

cooling or heating a region of the cavity having a high electric field intensity in order to promote the formation of a new phase in said region; and calculating a phase transition of the fluid within the cavity based on the detected changes in the resonant properties of the cavity.

44. A method of measuring the phase behavior of a fluid as defined in claim 43, the method further comprising the step of:

measuring the bulk density of the fluid and the density of one of the phases, which may be used to determine or obtain additional thermodynamic information from the measurements, such as the phase compositions of a mixture.

45. A method of measuring the phase behavior of a fluid as defined in claim 43, the method further comprising the step of:

measuring the location of impedance discontinuities within the cavity in order to determine the position of any liquid-vapor interface and hence the liquid volume.

46. A method of measuring the phase behavior of a fluid as defined in claim 43, the method further comprising the step of:

using the invariant features of the frequency signature (frequency vs temperature/pressure/density curve) of the fluid to calculate the liquid volume present.

* * * * *